United States Patent
Bates

(10) Patent No.: US 7,274,774 B2
(45) Date of Patent: Sep. 25, 2007

(54) DIGITAL ROTATION USING A SQUARE X-RAY DETECTOR AND A ROTATING COLLIMATOR

(75) Inventor: Daniel Mahonri Bates, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/247,660

(22) Filed: Oct. 11, 2005

(65) Prior Publication Data

US 2007/0081627 A1    Apr. 12, 2007

(51) Int. Cl.
  *G21K 1/02*    (2006.01)
(52) U.S. Cl. ........................ 378/147; 378/205
(58) Field of Classification Search ................ 378/148, 378/64, 150, 153, 65, 145, 147, 152, 205
  See application file for complete search history.

(56) References Cited

U.S. PATENT DOCUMENTS

| | | | |
|---|---|---|---|
| 4,991,189 A * | 2/1991 | Boomgaarden et al. ........ | 378/4 |
| 5,299,252 A * | 3/1994 | Takahashi ..................... | 378/50 |
| 6,907,105 B2 * | 6/2005 | Otto ............................. | 378/65 |
| 7,003,145 B2 * | 2/2006 | Polkus et al. ................ | 382/132 |

* cited by examiner

*Primary Examiner*—Hoon Song
(74) *Attorney, Agent, or Firm*—McAndrews, Held & Malloy, Ltd.; Peter J. Vogel; Michael A. Dellapenna

(57) ABSTRACT

Certain embodiments of the present invention provide a system, method and computer instructions for x-ray imaging. In an embodiment, such a system includes: an x-ray emission module configured to emit a stream of x-rays; a rotatable x-ray definition module configured to define the size and shape of the x-ray stream, wherein rotating the x-ray definition module rotates the shape of the x-ray stream; an x-ray detection module configured to detect the x-ray stream and create an image based on the detected x-rays; and an output module configured to output the image. In certain embodiments, the x-ray definition module may be configured to change the size of the x-ray stream when the x-ray definition module is rotated, for example. In certain embodiments, the x-ray detection module may be configured to rotate the image and/or change the size of the image before the image is output by the output module, for example.

21 Claims, 4 Drawing Sheets

DIGITAL ROTATION USING A SQUARE X-RAY DETECTOR AND A ROTATING COLLIMATOR

BACKGROUND OF THE INVENTION

The present invention generally relates to a system, method and computer instructions for x-ray imaging. More particularly, the present invention relates to a system method and computer instructions for x-ray imaging that allow an x-ray image created using a square x-ray detector to be readily rotated without losing portions of the radiated anatomy from the x-ray image.

X-rays are electromagnetic waves of short wavelength that are capable of penetrating some thickness of matter. Certain matter attenuates x-rays more than other types of matter. For example, x-rays directed at a body, such as a human body, are attenuated somewhat by body tissue, such as skin and muscle, more so by internal organs, such as lungs, and even more so by bones. Thus, by detecting x-rays that have passed through a body, an image of the internal structures of the body can be created.

Traditional x-ray imaging is comparable to a snapshot taken with an ordinary camera. A single, still image is created using film. Traditional x-ray imaging may be used for diagnostic purposes, such as diagnosing a broken bone, for example.

Another type of x-ray imaging called "fluoroscopy" is more like recording with a video camera. A continuous, possibly changing, image is created and displayed by continually detecting a stream of x-rays. Fluoroscopy may allow a physician to study moving body structures while performing surgery in an operating room, for example.

X-rays may be emitted from an x-ray source as an x-ray stream. Radiation absorbent material, such as lead or tungsten, may be used in devices that define the shape and size of an x-ray stream. One device that defines the shape and size of an x-ray stream is a collimator. A collimator may define the shape and size of an x-ray stream so that the stream is a circle or a square of a certain size, for example.

As mentioned above, an x-ray stream may be directed through a body to create an image of the internal structures of the body. The area of the body that the x-ray stream passes through may be referred to as "radiated anatomy" or the "exposed area" of the body. In order to detect x-rays after they have passed through a body, an x-ray detector may be situated such that the x-ray stream contacts the x-ray detector after it passes through the body. Further, an x-ray image may be created and/or displayed based on the x-rays that contact the x-ray detector.

Although x-rays may be useful in medicine, x-rays are also a type of radiation. Radiation may be harmful in certain doses. Thus, it is desirable to limit exposure to x-rays when possible.

In order to comply with United States Food and Drug Administration regulations, an x-ray detector should detect all x-rays that pass through a body, allowing for an image to be displayed that shows the entire radiated anatomy of the body. See 21 C.F.R. §1020.32. Further, in certain situations, an image that results from passing x-rays through a body may need to be rotated so that the image is presented in a certain orientation. Thus, x-ray imaging systems should meet two requirements: (1) an image of the entire "radiated anatomy" of a body should be detected and displayed; and (2) x-ray images should be readily rotated.

Circular collimators and corresponding circular x-ray detectors were once the norm in fluoroscopic x-ray imaging. Circular x-ray detectors utilized image intensifiers and image capture devices, such as cameras, to create and subsequently display x-ray images. When an x-ray image needed to be rotated, the device that captured the image was simply rotated. Because the collimator and the x-ray detector were both circular, and the image capture device created a circular image, the entire radiated anatomy could be shown in the image and the image could be rotated for display at any orientation.

Flat panel x-ray detectors have been developed. Flat panel x-ray detectors are advantageous because they create higher quality images than their round predecessors. The higher quality is due in part to integration of an image capture device into the detector, rather than utilizing an image intensifier and a camera.

However, flat panel detectors are not readily rotatable. This creates difficulty because the device that creates the image is no longer readily rotatable. Further, flat panel detectors are usually square in shape. This creates difficulty because, even if the detector was readily rotatable, rotating the detector may cause x-rays that have passed through certain radiated anatomy not to contact the detector, resulting in the creation of images that do not show all of the radiated anatomy.

Thus, there is a need for a system, method and computer instructions for x-ray imaging that allow an x-ray image created using a square x-ray detector to be readily rotated without losing portions of the radiated anatomy from the x-ray image.

BRIEF SUMMARY OF THE INVENTION

Certain embodiments of the present invention provide a system, method and computer instructions for x-ray imaging. In an embodiment, a system for x-ray imaging includes: an x-ray emission module configured to emit a stream of x-rays; a rotatable x-ray definition module configured to define the size and shape of the x-ray stream, wherein rotating the x-ray definition module rotates the shape of the x-ray stream; an x-ray detection module configured to detect the x-ray stream and create an image based on the detected x-rays; and an output module configured to output the image created by the x-ray detection module. In certain embodiments, x-ray definition module may be configured to: define the shape of the x-ray stream as a square; change the size of the x-ray stream when the x-ray definition module is rotated; and/or keep the size of the x-ray stream constant when the x-ray definition module is rotated, for example. In certain embodiments, the x-ray detection module may be configured to rotate the image and/or change the size of the image before the image is output by the output module, for example. In certain embodiments, the output module may be configured to output the image as a visual display, for example.

In an embodiment, a method for x-ray imaging includes: emitting a stream of x-rays; defining the shape and size of the x-ray stream; rotating the shape of the x-ray stream; detecting the x-ray stream; creating an image based on the detected x-ray stream; and outputting the image. In certain embodiments, the x-ray stream may be defined as a square, for example. In certain embodiments, the size of the x-ray stream may be changed when the shape of x-ray stream is rotated, for example. In certain embodiments, the size of the x-ray stream may remain constant when the shape of the x-ray stream is rotated, for example. In certain embodiments, the image may be rotated and/or the size of the image may be changed before the image is output, for example. In certain embodiments, the image may be output as a visual display, for example.

In an embodiment, a computer-readable storage medium includes a set of computer instructions for x-ray imaging. The set of instructions includes: an x-ray emission routine that allows a stream of x-rays to be emitted; an x-ray definition routine that allows the shape and size of the x-ray stream to be defined and the shape of the x-ray stream to be rotated; an x-ray detection routine that allows the x-ray stream to be detected and an image to be created based on the detected x-rays; and an output routine that allows the image to be output. In certain embodiments, the x-ray definition routine may allow: the shape of the x-ray stream to be square; the size of the x-ray stream to change when the shape of the x-ray stream is rotated; and/or the size of the x-ray stream to remain constant when the shape of the x-ray stream is rotated, for example. In certain embodiments, the x-ray detection routine may allow the image to be rotated and/or the size of the image to be changed before the output routine allows the image to be output, for example. In certain embodiments, the output routine allows the image to be output as a visual display, for example.

Figure 1:
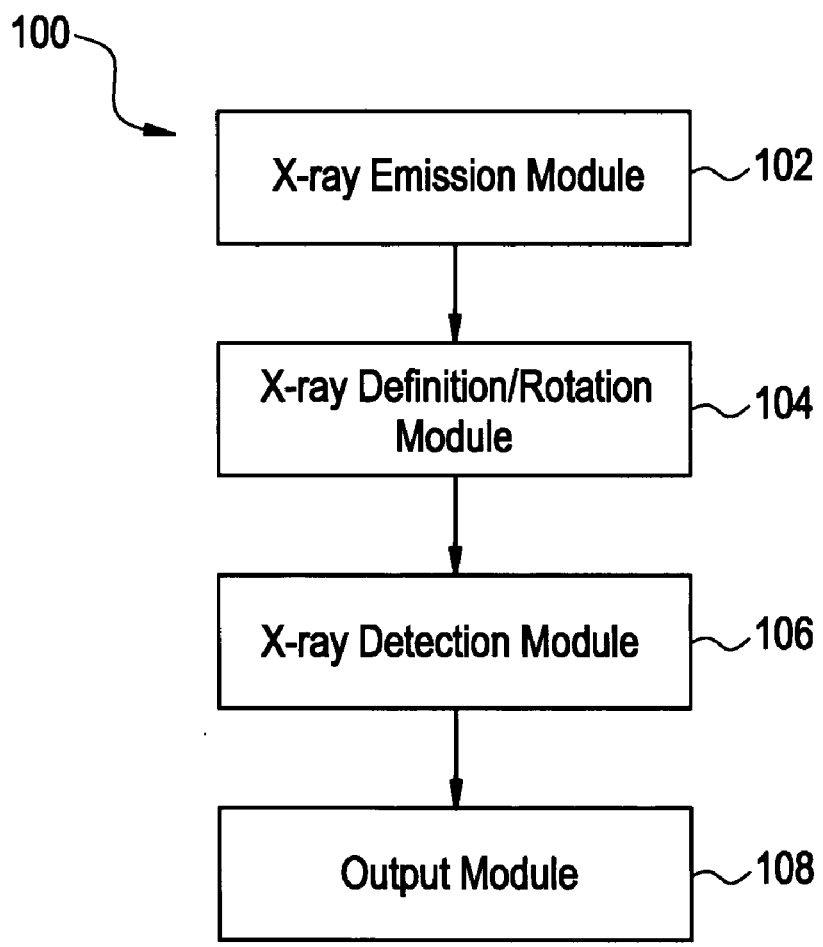
FIG. 1 illustrates a system for x-ray imaging used in accordance with an embodiment of the present invention.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

Figure 4:
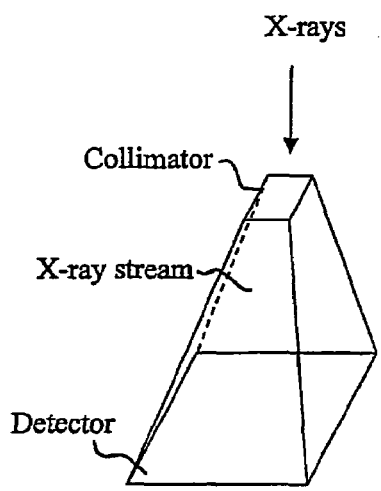

FIG. 4 illustrates a system for x-ray imaging used in accordance with an embodiment of the present invention.

Figure 5:
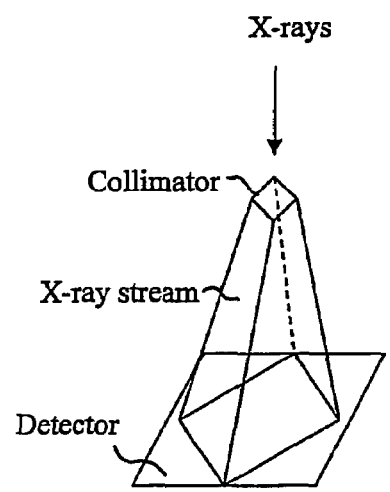

FIG. 5 illustrates a system for x-ray imaging used in accordance with an embodiment of the present invention.

Figure 6:
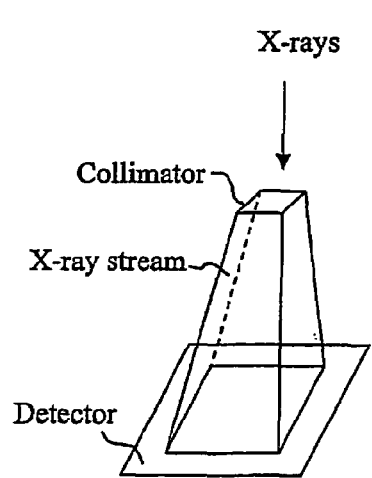

FIG. 6 illustrates a system for x-ray imaging used in accordance with an embodiment of the present invention.

Figure 7:
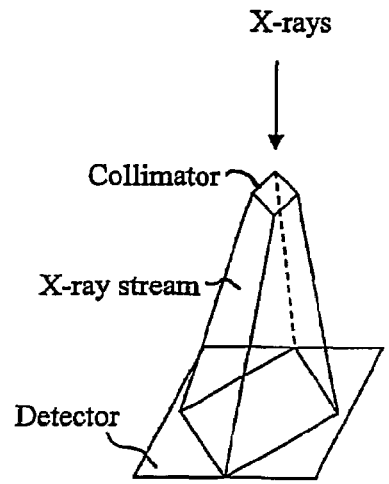

FIG. 7 illustrates a system for x-ray imaging used in accordance with an embodiment of the present invention.

DETAILED DESCRIPTION OF CERTAIN EMBODIMENTS

FIG. 1 illustrates a system for x-ray imaging used in accordance with an embodiment of the present invention. The system 100 in FIG. 1 includes an x-ray emission module 102 configured to emit a stream of x-rays; an x-ray definition/rotation module 104 configured to define the shape and size of the x-ray stream and rotate the shape of the x-ray stream; an x-ray detection module 106 configured to detect the x-ray stream and create an image based on the detected x-rays; and an output module 108 configured to output the image created by x-ray detection module 106.

In the system 100, the x-ray emission module 102 is configured to emit a stream of x-rays. For example, the x-ray emission module 102 may be configured to emit a stream of x-rays created by directing an electron beam at a target made of metal, such as Tungsten, for example. Other ways to configure the x-ray emission module 102 to emit a stream of x-rays may exist, as known to those skilled in the art.

In the system 100, the x-ray definition/rotation module 104 is configured to define the shape and size of the x-ray stream and rotate the shape of the x-ray stream. The x-ray definition/rotation module 104 may be configured to define the shape and size of the x-ray stream in many ways. For example, the x-ray definition/rotation module 104 may include a collimator, which may define the shape and size of the x-ray stream by only allowing x-rays within a certain boundary to pass through. Other ways to configure the x-ray definition/rotation module 104 to define the shape and size of an x-ray stream may exist, as known to those skilled in the art.

The x-ray definition/rotation module 104 may be configured to rotate the shape of the x-ray stream in many ways. For example, if the x-ray definition/rotation module 104 uses a collimator to define the shape and size of the x-ray stream, the collimator may be rotated in order to rotate the shape of the x-ray stream as depicted. for example, in FIGS. 4-7. Other ways to configure the x-ray definition/rotation module 104 to rotate the shape of the x-ray stream may exist, as known to those skilled in the art.

In one embodiment, the x-ray definition/rotation module 104 may be configured to change the size of the x-ray stream when the shape of the x-ray stream is rotated, as depicted, for example, in FIGS. 4 and 5. For example, if the x-ray stream is a square of a certain size, and the x-ray detector is an equally sized square, rotating the shape of the x-ray stream would cause certain x-rays to fall outside the area of the x-ray detector. To correct this, the size of the x-ray stream may be changed to be a smaller square when the shape of the x-ray stream is rotated. One way to achieve this is to have a rotating collimator that varies the size of the x-ray stream when the collimator rotates, as depicted, for example, in FIGS. 4 and 5. In this example, the collimator may allow the x-ray stream to be one size when the square x-ray stream is aligned with the square x-ray detector (as depicted, for example, in FIG. 4), and other, smaller, sizes when they are not aligned (as depicted, for example, in FIG. 5). A similar embodiment may be used any time either the shape of an x-ray stream or the shape of an x-ray detector is not circular.

In another embodiment, the x-ray definition/rotation module 104 may be configured to keep the size of the x-ray stream constant when the shape of the x-ray stream is rotated, as depicted, for example, in FIGS. 6 and 7. For example, if the x-ray stream is a square of a certain size, and the x-ray detector is large enough such that rotating the shape of the x-ray stream does not cause any x-rays to fall outside the area of the x-ray detector (as depicted, for example, in FIGS. 6 and 7), there is no need to change the size of the x-ray stream. A similar embodiment may be used any time the shape of an x-ray stream may be rotated without causing x-rays to fall outside the area of the x-ray detector.

In the system 100, the x-ray detection module 106 is configured to detect the x-ray stream and create an image based on detected x-rays. The x-ray detection module 106 may be configured to detect the x-ray stream and create an image based on detected x-rays using any type of x-ray detector and image creation device(s). For example, the x-ray detection module 106 may be configured to detect x-rays and create an x-ray image using an image intensifier and an image capture device, such as a camera. In another example, the x-ray detection module 106 may be configured to detect x-rays and create an x-ray image using an integrated x-ray detection and image creation system, such as the integrated x-ray detection and image creation systems used in connection with flat panel x-ray detectors. Other ways to configure the x-ray detection module 106 to detect x-rays and create an x-ray image may exist, as known by those skilled in the art.

The x-ray detection module 106 may be configured to include x-ray detectors of various shapes and sizes. For example, the x-ray detection module 106 may be configured to include a square x-ray detector or a circular x-ray detector of a certain size. The x-ray detection module 106 may be configured to include x-ray detectors of other shapes and sizes, as known to those skilled in the art.

The x-ray detection module 106 may be configured to rotate an x-ray image using digital image rotation. For example, an image created by the x-ray detection module 106 may be rotated from any orientation to any other orientation by applying digital image rotation. The x-ray detection module 106 may be configured to rotate an x-ray image in other ways, as known to those skilled in the art.

In an embodiment, the x-ray detection module 106 may be configured to rotate an x-ray image based on the rotation of the shape of an x-ray stream by the x-ray definition/rotation module 104. For example, if the x-ray definition/rotation module 104 rotates the shape of an x-ray stream 5 degrees clockwise, the x-ray detection module 106 may rotate the x-ray image 5 degrees counter-clockwise. Rotating an x-ray image in this manner may allow the x-ray image to be output in an orientation that is aesthetically pleasing to a viewer of the image. For example, if the x-ray stream, the x-ray image and a visual display that the x-ray image is to be output as are all square, and the x-ray stream has been rotated 5 degrees clockwise, in order for the x-ray image to be displayed in an orientation that is aesthetically pleasing, the x-ray image could be rotated 5 degrees counter-clockwise. Rotating a square x-ray image in this manner may allow the sides of the square x-ray image to be parallel to the sides of the square visual display when the x-ray image is displayed.

In an embodiment, the x-ray detection module 106 may be configured to enlarge an x-ray image. For example, if an x-ray image is smaller than a visual display that the x-ray image is to be output as, the x-ray detection module 106 may enlarge the x-ray image to fit the visual display.

In an embodiment, the x-ray detection module 106 may be configured to enlarge an x-ray image based on the reduction in size of an x-ray stream by the x-ray definition/rotation module 104. For example, if the x-ray definition/rotation module 104 reduces the size of an x-ray stream 5%, the x-ray detection module 106 may be configured to enlarge the x-ray image 5%. Enlarging an x-ray image that is output as a visual display in this manner may allow the x-ray image to fit the visual display.

In an embodiment, the x-ray detection module 106 may be configured to rotate and enlarge an x-ray image. For example, if a square x-ray image will be output as a square visual display, but the x-ray image is smaller than the display and was created at an orientation that does not align with the display, perhaps because the x-ray image was the result of an x-ray that was taken at an orientation that caused the size of the x-ray stream (and thus the size of the x-ray image) to be reduced, the image may be enlarged and rotated to fit the visual display. A similar embodiment may be used with any x-ray image that is smaller than a similarly shaped display and/or created at an orientation that does not align with the orientation of a similarly shaped display.

The output module 108 may be configured to output x-ray images in many ways. For example, the output module 108 may be configured to output x-ray images as a visual display and/or printed matter. It may be desirable to configure the output module 108 to output x-ray images in other ways, as known to those skilled in the art.

The modules of the system 100 may be implemented in many ways. For example, the modules may be implemented in hardware and/or software. The modules may be implemented separately and/or integrated in various combinations. It may be desirable to implement the modules of the system 100 in other ways, as known to those skilled in the art.

The system 100 may also be implemented in many ways. For example, the system 100 may be integrated with previously installed software applications as an add-on product. The system 100 may be integrated with x-ray imaging systems, such as a mobile c-arm system and/or a fixed room system, for example, that may be connected to a Hospital Information System (HIS) and/or a Radiology Information System (RIS). It may be desirable to implement the system 100 in other ways on other types of systems, as known to those skilled in the art.

In operation, the system 100 may be implemented in connection with an x-ray imaging system, such as a mobile c-arm system or a fixed room system. In such an embodiment, the x-ray emission module 102 may be configured so that an x-ray stream is emitted from an x-ray source. Then, as depicted, for example, in FIGS. 4-7, the x-ray stream may pass through the x-ray definition/rotation module 104 where a rotatable collimator may: (1) define the shape and size of the x-ray stream; and (2) rotate the shape of the x-ray stream while possibly varying the size of the x-ray stream, for example, to ensure that no x-rays fall outside the area of the x-ray detector. After the x-ray stream passes through the x-ray definition/rotation module 104, the x-ray stream may pass through any matter, such as body tissue, organs and/or bones, that exists between the x-ray definition/rotation module 104 and the x-ray detection module 106. Then, x-rays that have passed through such matter may contact the x-ray detection module 106, which may detect the x-rays and create an x-ray image using an integrated x-ray detection and x-ray image creation system, such as those used in connection with flat panel detectors, for example. The x-ray detection module 106 may then rotate (using digital image rotation) and/or enlarge the x-ray image so that it will fit in a visual display that the x-ray image is output as, for example. Finally, the output module 108 may output the x-ray image as a visual display and/or as printed matter, for example. The x-ray image may then be used to aid in surgery and/or for other purposes.

Figure 2:
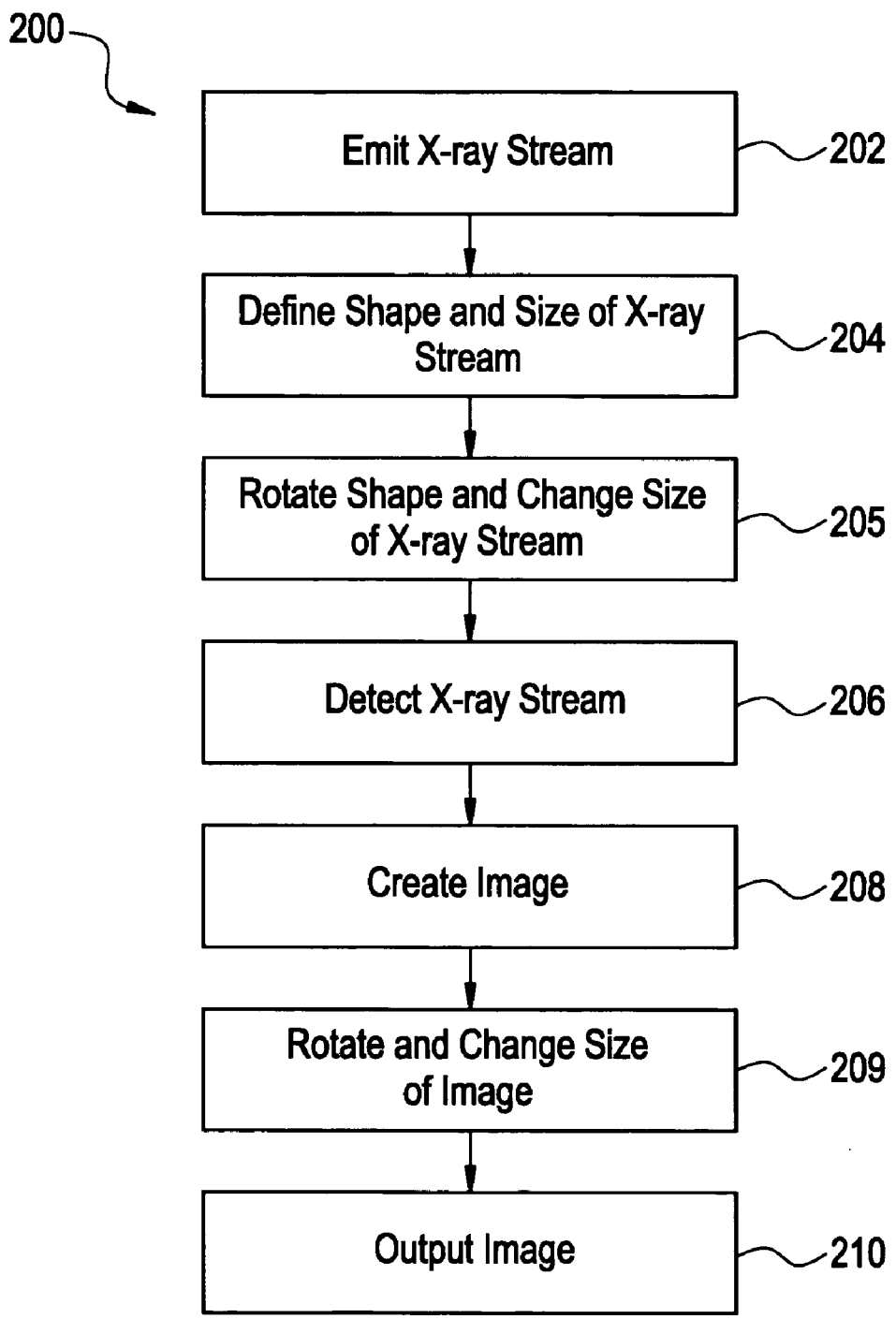
FIG. 2 illustrates a method for x-ray imaging used in accordance with an embodiment of the present invention.

FIG. 2 illustrates a method for x-ray imaging used in accordance with an embodiment of the present invention. At 202, an x-ray stream is emitted. For example, an x-ray source may emit a stream of x-rays. At 204, the shape and size of the x-ray stream is defined. For example, the x-ray stream may pass through a collimator that may define the shape and size of the x-ray stream. At 205, the shape of the x-ray stream may be rotated and the size of the x-ray stream may be changed. For example, the collimator that defines the shape and size of the x-ray stream may be rotatable, and may be rotated to rotate the shape of the x-ray stream while possibly varying the size of the x-ray stream, for example, to ensure that no x-rays fall outside the area of the x-ray detector. At 206, the x-rays are detected. For example, x-rays that have passed through body tissue, organs and/or bones may contact an x-ray detector. At 208, an x-ray image is created. For example, an x-ray image may be created using an integrated x-ray detection and x-ray image creation system, such as those used in connection with flat panel detectors. At 209, an x-ray image is rotated and the size of the x-ray image is changed. For example, the x-ray image may be rotated (using digital image rotation) and/or enlarged so that it will fit in a visual display of a certain size. At 210, the x-ray image is output. For example, the x-ray image may be output as visual display and/or printed matter.

Due to the difficulty of rotating square flat panel x-ray detectors, obtaining x-ray images at certain orientations that show the entire "radiated anatomy" has become a challenge. Applying the method 200, as described above and/or in light of the description of FIG. 1, may allow x-ray images created using square and/or other non-circular x-ray detectors to be readily rotated without losing portions of the "radiated anatomy" from the x-ray image.

Figure 3:
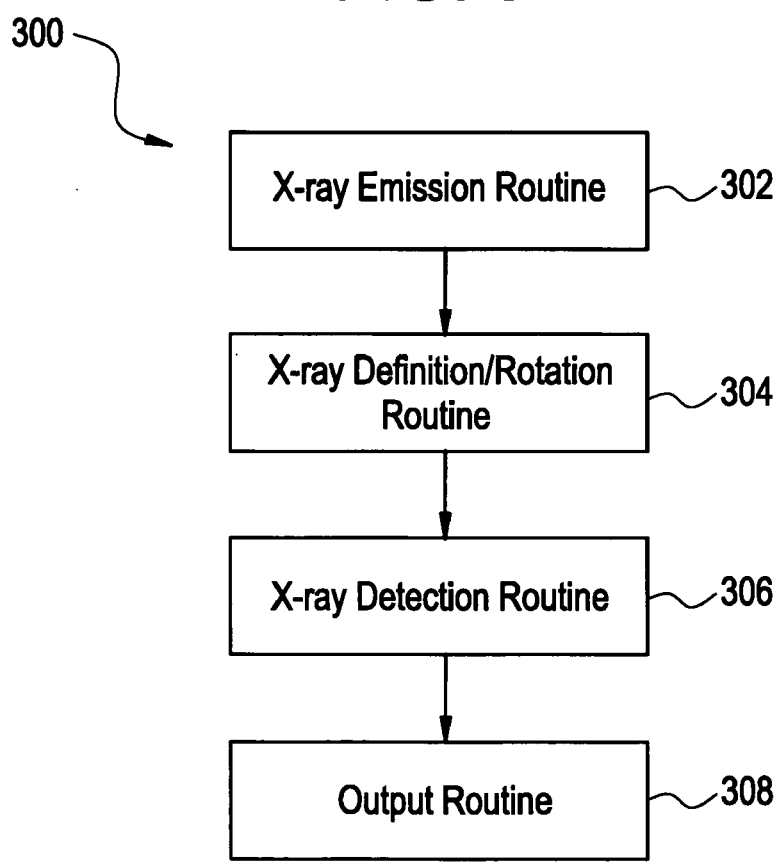
FIG. 3 illustrates a set of computer instructions for x-ray imaging used in accordance with an embodiment of the present invention.

FIG. 3 illustrates a set of computer instructions 300 for x-ray imaging used in accordance with an embodiment of the present invention. The set of computer instructions 300 in FIG. 3 includes an x-ray emission routine 302, which allows a stream of x-rays to be emitted; an x-ray definition/ rotation routine 304, which allows the size and shape of the x-ray stream to be defined and the shape of the x-ray stream to be rotated; an x-ray detection routine 306, which allows the x-ray stream to be detected and an image to be created based on the detected x-rays; and an output routine 308, which allows the image created by the x-ray detection routine 306 to be output.

In an embodiment, the x-ray emission routine 302, the x-ray definition/rotation routine 304, the x-ray detection routine 306, and the output routine 308 may be implemented and/or may perform functions similar to the x-ray emission module 102, the x-ray definition/rotation module 104, the x-ray detection module 106 and the output module 108, respectively, as described above in relation to FIG. 1.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An x-ray imaging system comprising:
   an x-ray emission module configured to emit a stream of x-rays;
   an x-ray detection module configured to detect the x-ray stream, wherein the x-ray detection module includes a rectangular detector; and
   a rotatable collimator configured to define the shape and size of the x-ray stream, wherein the collimator is configured to define the shape of the x-ray stream to be rectangular, wherein rotating the collimator rotates the shape of the x-ray stream and changes the size of the x-ray stream, wherein the x-ray stream is a size when the shape of the x-ray stream is aligned with the shape of the detector, and wherein the x-ray stream is a smaller size when the shape of the x-ray stream is not aligned with the shape of the detector.

2. The system of claim 1, wherein the collimator is configured to define the shape of the x-ray stream as a square.

3. The system of claim 1, wherein the x-ray detection module is configured to create an image based on the detected x-rays.

4. The system of claim 3, further comprising an output module configured to output the image created by the x-ray detection module.

5. The system of claim 4, wherein the x-ray detection module is configured to rotate the image before the image is output by the output module.

6. The system of claim 4, wherein the x-ray detection module is configured to change the size of the image before the image is output by the output module.

7. The system of claim 4, wherein the output module is configured to output the image as a visual display.

8. A method for x-ray imaging comprising:
   emitting a stream of x-rays;
   defining the shape and size of the x-ray stream using a collimator;
   defining the shape of the x-ray stream to be rectangular;
   rotating the shape of the x-ray stream by rotating the collimator;
   changing the size of the x-ray stream as the collimator is rotated such that the x-ray stream is a size when the shape of the x-ray stream is aligned with the shape of a rectangular detector and the x-ray stream is smaller when the shape of the x-ray stream is not aligned with the shape of the rectangular detector; and
   detecting the x-ray stream using the rectangular detector.

9. The method of claim 8, wherein the x-ray stream is defined by the collimator as a square.

10. The method of claim 8, further comprising creating an image based on the detected x-ray stream.

11. The method of claim 10, further comprising outputting the image.

12. The method of claim 11, wherein the image is rotated before being output.

13. The method of claim 11, wherein the size of the image is changed before being output.

14. The method of claim 11, wherein the image is output as a visual display.

15. A computer-readable storage medium including a set of computer instructions for x-ray imaging, the set of instructions comprising:
   an x-ray emission routine that allows a stream of x-rays to be emitted;
   an x-ray detection routine that allows the x-ray stream to be detected using a rectangular detector; and
   an x-ray definition routine that allows the shape and size of the x-ray stream to be defined by a collimator, wherein the x-ray definition routine allows the collimator to define the shape of the x-ray stream to be rectangular, wherein the x-ray definition routine allows the collimator to rotate the shape of the x-ray stream and change the size of the x-ray stream when the collimator is rotated, wherein the x-ray definition routine allows the collimator to make the x-ray stream a size when the shape of the x-ray stream is aligned with the shape of the detector, and wherein the x-ray definition routine allows the collimator to make the x-ray stream a smaller size when the shape of the x-ray stream is not aligned with the shape of the detector.

16. The set of instructions of claim 15, wherein the x-ray definition routine allows the collimator to define the shape of the x-ray stream to be square.

17. The set of instructions of claim 15, wherein the x-ray detection routine allows an image to be created based on the detected x-rays.

18. The set of instructions of claim 17, further comprising an output routine that allows the image to be output.

19. The set of instructions of claim 18, wherein the x-ray detection routine allows the image to be rotated before the output routine allows the image to be output.

20. The set of instructions of claim 18, wherein the x-ray detection routine allows the size of the image to be changed before the output routine allows the image to be output.

21. The set of instructions of claim 18, wherein the output routine allows the image to be output as a visual display.

* * * * *